United States Patent [19]

Kuck

[11] 3,987,118
[45] Oct. 19, 1976

[54] NOVEL PROCESS FOR THE OXYCHLORINATION OF ETHANE

[75] Inventor: Mark Allen Kuck, Montclair, N.J.

[73] Assignee: Stauffer Chemical Company, Westport, Conn.

[22] Filed: Apr. 30, 1973

[21] Appl. No.: 355,857

Related U.S. Application Data

[63] Continuation-in-part of Ser. No. 122,203, March 8, 1971, abandoned.

[52] U.S. Cl. .................. 260/654 A; 260/656 R; 260/659 A; 260/662 A
[51] Int. Cl.² .......................................... C07C 21/04
[58] Field of Search ........ 260/654 A, 659 A, 662 A, 260/656 R

[56] References Cited
UNITED STATES PATENTS

| | | | |
|---|---|---|---|
| 3,360,483 | 12/1967 | Diamond | 252/441 |
| 3,407,039 | 10/1968 | Bryant | 260/659 A |
| 3,546,306 | 12/1970 | McCarthy | 260/654 A |
| 3,642,918 | 2/1972 | Bohl et al. | 260/654 A |

FOREIGN PATENTS OR APPLICATIONS

| | | | |
|---|---|---|---|
| 721,783 | 11/1965 | Canada | 260/654 A |
| 1,049,213 | 11/1966 | United Kingdom | 260/654 A |

OTHER PUBLICATIONS

Chemical Week, pp. 81 and 82, (Nov. 14, 1964).
Addison et al., J. Chem. Soc., 759, (1955).

Primary Examiner—Delbert E. Gantz
Assistant Examiner—Joseph A. Boska
Attorney, Agent, or Firm—Daniel S. Ortiz

[57] ABSTRACT

There is disclosed a process for the oxychlorination of ethane which comprises reacting a gaseous mixture of ethane, oxygen and a chlorination agent such as hydrogen chloride, preferably in a fluidized bed, while in the presence of a copper substituted faujasite Y catalyst so as to produce a product containing a mixture of chlorinated hydrocarbons selected from the group consisting of cis 1,2-dichloroethylene, 1,1-dichloroethane, 1,2-dichloroethane, trichloroethylene, vinyl chloride and perchloroethylene.

18 Claims, No Drawings

NOVEL PROCESS FOR THE OXYCHLORINATION OF ETHANE

CROSS REFERENCE TO RELATED APPLICATION

This application is a continuation in part of copending application Ser. No. 122,203, filed Mar. 8, 1971, now abandoned.

BACKGROUND OF THE INVENTION

As is well known to those skilled in the art, an oxychlorination process involves the reaction between a hydrocarbon, oxygen and a chlorination agent, usually hydrogen chloride, to produce chlorinated hydrocarbons.

A typical process for the oxychlorination of ethane is the modified Deacon type chlorination procedure in which the ethane is chlorinated, at elevated temperatures, with hydrogen chloride and an oxygen containing gas, such as air or elemental oxygen, in the presence of a metal halide catalyst such, for example, as cupric chloride/aluminum oxide. In this process, the first step in the reaction is believed to involve the oxidation of the hydrogen chloride in the presence of the catalyst so as to form chlorine and water whereupon, in the second step of the reaction, the chlorine which is liberated from the hydrogen chloride reacts with the ethane which is present in the feed gas so as to form chlorinated hydrocarbons, of which ethyl chloride is a principal component, and additional hydrogen chloride. The hydrogen chloride produced by this second step in the reaction is then oxidized as part of the first step in the reaction process and the resulting chlorine reacts with additional ethane.

In a modification of the above described ethane oxychlorination process, elemental chlorine is used as the chlorination agent and the hydrogen chloride is generated by the chlorination of the ethane and fed, together with the elemental chlorine, to the catalytic reaction zone. Thus, free chlorine, an oxygen containing gas, such as air or oxygen, and ethane are brought into contact with a metal halide catalyst maintained at elevated temperatures. The chlorine reacts with the ethane so as to produce hydrogen chloride and chlorinated derivatives of the ethane of which ethyl chloride is the major component. The chlorine content of the hydrogen chloride which is produced in this manner is then utilized to achieve additional chlorination of the ethane feed by means of a standard Deacon type reaction, as described hereinabove, in which the hydrogen chloride is oxidized to form water and elemental chlorine.

TECHNICAL DISCLOSURE OF THE INVENTION

It has now been discovered that the use of a copper substituted faujasite Y catalyst, as hereinafter described, in the oxychlorination of ethane, preferably in a fluidized bed reactor, leads to the surprising result of providing a chlorinated hydrocarbon product mixture in which the major or predominant components, on a molar basis of the chlorocarbons produced are 1,1-dichloroethane, vinyl chloride, cis 1,2-dichloroethylene, 1,2-dichloroethane, trichloroethylene and perchloroethylene with the trichloroethylene and perchloroethylene accounting for a substantial portion of the total chlorocarbons which are produced. This result is, therefore, in marked contrast to the results obtained in oxychlorinating ethane in the presence of the supported metal halide catalysts of the prior art which yield ethyl chloride as a principal product of the reaction. Thus, it is to be emphasized that the novel process of this invention leads to the preferential formation of olefinic chlorocarbons in contrast to the results obtained when ethane is oxychlorinated in the presence of the supported metal halide catalysts of the prior art where, under similar reaction conditions, saturated chlorocarbons are the principal products.

As has been noted, the preferred embodiment of this novel ethane oxychlorination process involves the use of a fluidized bed reactor. As is known to those skilled in the art, and as used herein, the term "fluidized bed" refers to a process in which a gas is passed upwardly through a bed of finely divided, solid catalyst containing particles. When the gas is passed through a bed of solid particulate material in this manner, several different conditions may be established depending upon the gas velocities employed, the size of the particles used, and other similar considerations. Thus, if the gas velocities are relatively low, the bed of solid particles remains essentially static and the gas simply passes through the bed without any changes taking place other than a slight expansion of the bed. On the other hand, as the gas velocity is increased, at least some of the particles become dynamically suspended in the upwardly rising gas stream. As a result, the height of the bed expands. Such beds are termed "dynamic beds." If the gas velocity is increased, still further, all of the particles become suspended in the gas and the bed undergoes additional expansion. Ultimately, the bed may assume a highly turbulent condition which in many ways resembles a boiling liquid.

The present process is concerned with conducting reactions in catalyst beds with gas velocities which provide for dynamic and fluidized beds. The exact conditions requisite to establishing such bed conditions depend upon such factors as the particle size and distribution of sizes of the bed particles, the components of the feed, the gas velocity, the density of the particles and other like considerations. Wilhelm and Kwauk, "Chemical Engineering Progress", Vol. 44, page 201 (1948), equate the various factors necessary for fluidizing a bed and by following the principles therein discussed, the desired bed conditions may be provided for. In the preferred mode of operating the instant process, a fluidized bed rather than a dynamic bed is employed.

In accordance with the present invention, by the proper selection of conditions, such as catalyst particle size and density, bed height, fluidizing velocities and other similar considerations, the major portion of the oxychlorination reaction is caused to take place in the lower portion of the fluidized bed, while the remaining upper portion of the fluidized bed is operated under conditions designed to cool the particles which are heated by the exothermic reaction taking place in the lower portion of the fluidized bed. Operation in this manner provides excellent conversion of feed material during the oxychlorination of ethane by means of the process of this invention.

In greater detail, now, the present invention provides a process for the production of chlorinated hydrocarbons by the oxychlorination of ethane. In this process, a feed comprising a vapor phase mixture of ethane, a chlorinating agent which is, preferably, hydrogen chloride, and an oxidizing agent, such as oxygen, the oxygen which is present as a component of air or a mixture of oxygen and nitrogen, are reacted by being passed through a fluid bed in which the novel catalyst of the present invention, that is, a copper substituted faujasite Y material, is incorporated. This feedstock mixture is passed through the bed at a temperature ranging between 250° and 500° C. and preferably 300° to 450° C. over a retention time range longer than 2 seconds and preferably from about 5 to 10 seconds so as to produce a chlorinated hydrocarbon product mixture whose major components are 1,1-dichloroethane, 1,2-dichloroethane, perchloroethylene, trichloroethylene, vinyl chloride and cis 1,2-dichloroethylene. And, as noted earlier, a significant aspect of this novel process is the fact that the trichloroethylene and the perchloroethylene account for a substantial portion of the total yield of chlorocarbons.

The catalyst useful in the practice of the present invention directs the chlorination of hydrocarbons containing more than one carbon atom to the formation of major proportions of polychlorinated and olefinic chlorinated hydrocarbons under reaction conditions at which prior art catalysts form monochlorinated or polychlorinated paraffinic materials.

It is then desirable to cool this product in order to remove the heat which has been generated by the exothermic reactions involved in the oxychlorination of ethane by means of this novel process.

In carrying out the process, an effective concentration of the catalyst is incorporated in the fluidized bed whereupon a vapor phase mixture of oxygen, hydrogen chloride and ethane is passed through the bed at a rate sufficient to provide for the reaction between the ethane, the oxygen and the chloride content of the hydrogen chloride. In this process it is desired to provide a conversion, to chlorinated hydrocarbons, of at least about 40% of the chlorine values of the hydrogen chloride or other chlorinating agent.

The copper substituted faujasite Y catalysts which are applicable for use in the process of this invention are the sodium synthetic faujasites having the unit cell composition $Na_{56}[(AlO_2)_{56}(SiO_2)_{136}] \cdot 25 H_2O$ in which from about 0.2 to about 8%, by weight, of the composition comprises divalent copper ions which have been introduced into the faujasite composition by means of a conventional ion exchange reaction whereby the copper ions are substituted for the sodium ions of the faujasite. If desired, there may be one or more other species of polyvalent metal ions present in the catalyst provided, however, that it still contains at least 0.2%, by weight, of the divalent copper ions. These optional polyvalent metal ions may include alkaline earth metal ions such as $Mg^{++}$ and $Ca^{++}$, transition metal ions such as $Fe^{+++}$ and $Ni^{++}$, and rare earth ions such as $Ce^{+++}$ and $La^{+++}$. However, it is to be noted that the use of a sodium faujasite Y catalyst which has been substituted only with divalent copper ions is preferred for use in the oxychlorination process of this invention.

A conventional method for preparing sodium synthetic faujasite Y materials which can then be used in preparing the above described copper substituted catalysts involves a process wherein colloidal silica or silica hydrosol is first mixed with a solution of sodium hydroxide and sodium aluminate at ambient temperature. Suitable reactant molar ratios are within the following ranges: $NaO/SiO_2$, 0.28 to 0.80; $SiO_2/Al_2O_3$, 7 to 40; $H_2O/Na_2O$, 20 to 60. The reaction mixture is preferably allowed to digest at ambient temperature for up to 40 hours or more, preferably 1 to 15 hours, in order to aid crystallization after which it is heated at 180° to 250° F., e.g., 200° to 220° F., for a sufficient period to crystallize the product and to achieve maximum crystallinity, e.g., 24 to 200 hours or more, typically 50 to 100 hours. A crystalline hydrated sodium alumino-silicate zeolite having a faujasite structure is then separated from the aqueous mother liquor by decantation or filtration, washed, and dried to recover a crystalline product. It may then be finally calcined at temperatures up to about 1000° F. in order to remove the water of hydration and thereby form interstitial channels which confer adsorptive and catalytic properties.

Thereafter, in preparing the copper substituted faujasite Y catalyst used in the subject process from the sodium synthetic faujasite Y, the procedure which is ordinarily followed involves the treatment of an aqueous slurry of the thus prepared sodium synthetic faujasite Y, which has been adjusted to a pH of 5.5–6.0, with an aqueous solution of cupric acetate. The resulting mixture is maintained at ambient temperatures, without stirring, for about 30 minutes. It is then filtered and the resulting filter cake is calcined at about 400° C. for about 18 hours where it is desired to prepare these catalysts so that they contain one or more polyvalent metal ions in addition to the required divalent copper ions, the thus prepared copper substituted material is put into the form of an aqueous slurry into which a solution of a salt of the selected polyvalent metal ion is introduced followed by filtration and calcining. This same procedure is then repeated with as many polyvalent metal salt solutions as is desired.

It is to be noted, at this point, that the above described catalysts, as is shown by X-ray diffraction patterns, retain their crystalline zeolite structures without any substantial alteration during the ethane oxychlorination process of this invention.

As has been noted, the selected oxidizing agent may be pure oxygen, air or mixtures of oxygen and nitrogen. The primary and certainly the preferred chlorinating agent for use in this process is hydrogen chloride. Chlorine may also be used either in a pure state or in a mixture with hydrogen chloride. However, the use of hydrogen chloride is preferred because of its low cost and ready availability. The oxychlorination of the ethane in the process of this invention generally takes place at a temperature beween about 300° and 500° C. over a retention time range, i.e. the time during which the reactants are in contact with the catalyst, of at least 2 seconds and preferably from about 5 to 10 seconds. Larger contact times are not harmful to the process and tend to promote reaction of the HCl. It should be stressed, at this point, that the latter process conditions, as well as the below described proportions and flow rates, are merely illustrative and may be varied if so desired by the practitioner in order to produce the chlorinated products in the required ratio or to suit the particular apparatus or other criteria relevant to his successful carrying out of the oxychlorination procedure of this invention.

The proportions of the various reagents and the concentration of the catalyst which are used in the process of this invention are largely dependent upon the particular catalyst which is utilized.

The high proportion of polychlorinated ethane and ethylene and the low level of ethyl chloride in the reaction mixture is observed at reactor inlet molar ratios of ethane to HCl as high as 5:2. As the molar ratio of ethane to HCl in the feed is reduced a larger proportion of the ethane can be reacted but the reaction mixture contains only small amounts of ethyl chloride. The ratios of reactant feed to the oxychlorination zone can range from an ethane:HCl molar ratio of between about 5:2 to about 1:3 and an oxygen:HCl molar ratio between about 2:1 to about 1:3. Usually the molar ratio of oxygen:HCl is not below about 1:2.

The reactants must be fed into the fluid bed at a rate sufficient to maintain the catalyst bed in the fluid state. The proper choice of flow rate is quite significant since the use of too high a flow rate will result in a loss of catalyst while the use of too low a flow rate will preclude proper fluidization of the bed. The fluidized bed reactor will generally have a suitable porous support for the catalyst. The mixture of the reactants can be preheated to the desired reaction temperature prior to entering the bed but, in view of the excellent heat transfer characteristics of a fluid bed preheating is not necessary. Suitable means for maintaining the reactor at a constant temperature should be provided. In addition, it is often convenient to introduce the mixture of gaseous reactants, i.e. the mixture of hydrogen chloride, ethane and oxygen, into the reactor in an inert gas carrier. The use of nitrogen is preferred for this purpose.

The following examples will further illustrate the embodiment of this invention. In these examples all parts given are by weight unless otherwise noted.

EXAMPLE I

This example illustrates the preparation of a copper substituted faujasite Y material suitable for use as a catalyst in the process of this invention.

A 100 gram sample of a sodium synthetic faujasite Y material, sold by the Linde Division of Union Carbide Corporation as "Linde Molecular Sieve SK-40" is washed with distilled water and dried at 110° C. It is then transferred to a beaker to which there has previously been added 600 milliliters of distilled water. The pH of the resultant mixture is about 10 and is, therefore, adjusted to a value of about 5.75 by the addition of acetic acid.

A total of 200 milliliters of 0.1M cupric acetate is then added to the mixture which is maintained, without stirring, for about 10 minutes. At this time, a second addition of 200 milliliters of the 0.1M cupric acetate is made and after 20 minutes the mixture is filtered. The resulting filter cake is transferred to a beaker and 300 milliliters of 0.1M cupric acetate is added. This mixture is maintained at a temperature of about 25° C. without stirring for a period of about 22 hours and the resulting slurry is then filtered. Finally, the resulting filter cake is calcined at 405° C. for 18 hours yielding a copper substituted faujasite Y material in which about 4%, by weight, of the material comprises divalent copper ions.

EXAMPLE II

Part I

A gaseous mixture of hydrogen chloride, ethane, oxygen, and nitrogen in a mole ratio of about 1:1:1:2 is preheated to about 400° C. and passed through a fluidized bed reactor maintained at 400° C. containing 15 grams of the copper substituted synthetic faujasite Y catalyst whose preparation is described, hereinabove, in Example I. The bed is maintained on a porous support of glass frit in a reactor vessel having a diameter of 25mm and a length of 60mm. The flow of the feed mixture through the reactor is at the rate of about 300 ml/minute and the total retention time of the feed in the reactor is about 6 seconds. The reactor is submerged in a thermostatically controlled molten salt bath which is continuously stirred to assure a constant temperature throughout the bath. The temperature of both the bath and the reactor are monitored with appropriate thermocouples which are connected to a multipoint recorder. The product stream passes from the reactor through a heated Pyrex line and the thus heated stream is periodically sampled and analyzed by gas chromatography.

After the removal of water from the system it is determined that the conversion level of the hydrogen chloride to chlorinated hydrocarbons is about 41%. The thus prepared chlorinated hydrocarbons comprise a mixture of twelve components of which as based on area % trapped at −79° C., six components are found to account for more than 95% of the total. The following table lists these six major components of the product mixture and the molar concentration in which they are present therein.

PRODUCT DISTRIBUTION OF THE MAJOR CHLORINATED HYDROCARBONS RESULTING FROM THE OXYCHLORINATION OF ETHANE USING A COPPER SUBSTITUTED FAUJASITE Y CATALYST

| Compound | Molar Concentration %* |
|---|---|
| 1,1-dichloroethane | 19 |
| cis 1,2-dichloroethylene | 26 |
| 1,2-dichloroethane | 8 |
| trichloroethylene | 19 |
| perchloroethylene | 23 |
| vinyl chloride | 2 |

*Based on area % of material trapped at −79° C. determined by gas chromatography analysis.

PART 2

Three repetitions of the reaction procedure described in Part 1, hereinabove, are carried out wherein, in each case, the input ratio of the components of the feed mixture is varied in order to determine the effect of such variations upon the conversion level of the hydrogen chloride as well as upon the distribution of the various components of the product stream. The following table indicates the input ratio, on a molar basis, of the reactants in each feed stream, the % hydrogen chloride converted and the molar concentration of the major components which are found in the product stream. The reactor was maintained at 400° C. during the three runs.

| | | | MOLAR CONCENTRATION OF CHLOROCARBON PRODUCT COMPONENTS* | | | | | |
|---|---|---|---|---|---|---|---|---|
| Run No. | Input Ratio $O_2:N_2:HCl:C_2H_6$ | % HCl Converted | Vinyl Chloride | 1,1-dichloro- Ethane | cis 1,2-dichloro- Ethylene | 1,2-dichloro- Ethane | Trichloro- Ethylene | Perchloro- Ethylene |
| 1 | 1:2:1:2 | 53 | 5 | 18 | 25 | 6 | 21 | 23 |
| 2 | 2:3.6:2:1 | 67 | 2 | 21 | 28 | 6 | 17 | 21 |

-continued

MOLAR CONCENTRATION OF CHLOROCARBON PRODUCT COMPONENTS*

| Run No. | Input Ratio $O_2:N_2:HCl:C_2H_6$ | % HCl Converted | Vinyl Chloride | 1,1-dichloro-Ethane | cis 1,2-dichloro-Ethylene | 1,2-dichloro-Ethane | Trichloro-Ethylene | Perchloro-Ethylene |
|---|---|---|---|---|---|---|---|---|
| 3 | 1.5:1:1:1.5 | 81 | 10 | 19 | 25 | 9 | 18 | 16 |

*Based on area % of material trapped at −79° C. determined by gas chromatography analysis.

The above data reveal that the process of this invention provides for a high level of chlorination at all input ratios including the low HCl input in Run No. 3, where the combined molar concentration of the trichloroethylene and the perchloroethylene account for 49% of the HCl which reacts as well as in Run No. 1, which contains a high ratio of ethane, and wherein the combined molar concentration of the trichloroethylene and the perchloroethylene accounts for 60% of the HCl undergoing reaction.

EXAMPLE III

This example again illustrates the ethane oxychlorination process of this invention which, in this case, is carried out using, as a catalyst, a synthetic faujasite Y material which has been substituted with about 1.4%, by weight, of divalent copper ions and with about 2.3%, by weight, of $Ca^{++}$ ions.

A gaseous mixture of hydrogen chloride, ethane, oxygen, and nitrogen in a mole ratio of about 1:1:1:2 is preheated to about 350° C. and passed through a fluidized bed reactor maintained at 350° C. containing 15 grams of a catalyst comprising a synthetic faujasite Y material which has been substituted with 1.4%, by weight, of divalent copper ions and with about 2.3%, by weight, of $Ca^{++}$ ions. The bed is maintained on a porous support of glass frit in a reactor vessel having a diameter of 25mm and a length of 60mm. The flow of the feed mixture through the reactor is at the rate of about 300 ml/minute and the total retention time of the feed in the reactor is about 6 seconds. The reactor is submerged in a thermostatically controlled molten salt bath which is continuously stirred to assure a constant temperature throughout the bath. The temperature of both the bath and the reactor are monitored with appropriate thermocouples which are connected to a multipoint recorder. The product stream passes from the reactor through a heater Pyrex line and the thus heated stream is periodically sampled and analyzed by gas chromatography.

After the removal of water from the system, it is determined that the conversion level of the hydrogen chloride to chlorinated hydrocarbons is about 41%. The thus prepared chlorinated hydrocarbons comprise a mixture of twelve components of which, as based on area % trapped at −79° C., six components are found to account for more than 95% of the total. The following table lists these six major components of the product mixture and the molar concentration in which they are present therein.

PRODUCT DISTRIBUTION OF THE MAJOR CHLORINATED HYDROCARBONS RESULTING FROM THE OXYCHLORINATION OF ETHANE USING A COPPER SUBSTITUTED FAUJASITE Y CATALYST

| Compound | Molar Concentration %* |
|---|---|
| 1,1-dichloroethane | 18 |
| cis 1,2-dichloroethylene | 27 |
| 1,2-dichloroethane | 8 |
| trichloroethylene | 17 |
| perchloroethylene | 26 |
| vinyl chloride | 2 |

*Based on area % of material trapped at −79° C. determined by gas chromatography analysis.

Variations may be made in proportions, procedures and materials without departing from the scope of this invention as defined in the following claims.

What is claimed is:

1. In a process for the preparation of chlorinated hydrocarbons by the oxychlorination of ethane wherein ethane, oxygen and a chlorination agent selected from the group consisting of hydrogen chloride, chlorine and mixtures thereof are reacted at a temperature between about 250° C. and about 500° C. while in contact with a catalyst, the improvement which comprises the use as a catalyst, for said reaction of a copper substituted sodium faujasite Y material containing from about 0.2 to 8%, by weight, of divalent copper ions.

2. The process of claim 1, wherein said catalyst contains about 4%, by weight, of divalent copper ions.

3. The process of claim 1, wherein said catalyst contains at least one optional species of polyvalent metal ions in addition to said divalent copper ions, said optional species of polyvalent metal ions being selected from the group consisting of alkaline earth, transition metal and rare earth ions and mixtures thereof.

4. The process of claim 3, wherein said optional species of polyvalent metal ions is $Ca^{++}$.

5. The process of claim 1, wherein said reaction is conducted in a fluidized bed reactor.

6. The process of claim 1, wherein said reaction is conducted at a temperature in the range of from about 300–450° C.

7. The process of claim 1, wherein the oxygen which is used in said reaction is pure oxygen.

8. The process of claim 1, wherein the oxygen which is used in said reaction is present as a component of air.

9. The process of claim 1, wherein the oxygen which is used in said reaction is present as part of a mixture of nitrogen and oxygen.

10. The process of claim 1, wherein said chlorinating agent is hydrogen chloride.

11. The process of claim 1, wherein said chlorinating agent is chlorine.

12. The process of claim 1, wherein said chlorinating agent is a mixture of hydrogen chloride and chlorine.

13. The process of claim 10, wherein the retention time during which said ethane, oxygen and hydrogen chloride are in contact with said catalyst is from about 5 to 10 seconds.

14. The process of claim 10, wherein said oxygen, hydrogen chloride and ethane enter said reaction in a molar ratio of ethane to HCl of from about 5:2 to about 1:3 and an oxygen to HCl ratio of from about 2:1 to about 1:3.

15. The process of claim 1, wherein said ethane, oxygen and chlorination agent are present, during said reaction, as a mixture in an inert gas carrier.

16. The process of claim 15, wherein said inert gas carrier is nitrogen and said chlorination agent is hydrogen chloride.

17. The process of claim 1, wherein the chlorinated hydrocarbons resulting from said reaction comprise a mixture whose major components are 1,1-dichloroethane, cis 1,2-dichloroethylene, 1,2-dichloroethane, trichloroethylene, vinyl chloride and perchloroethylene.

18. The process of claim 17, wherein trichloroethylene and perchloroethylene comprise at least 40%, on a molar basis, of the mixture of chlorinated hydrocarbons resulting from said reaction.

* * * * *